United States Patent [19]

Kashiwaba et al.

[11] Patent Number: 4,988,828
[45] Date of Patent: Jan. 29, 1991

[54] PHENOXYPROPYL DERIVATIVES

[75] Inventors: Noriaki Kashiwaba, Kawasaki; Hajime Matsumoto, Hino; Akihiko Hosoda, Shiki; Yasuo Sekine, Yokohama, all of Japan

[73] Assignee: Fujirebio Kabushiki Kaisha, Tokyo, Japan

[21] Appl. No.: 275,375

[22] Filed: Nov. 23, 1988

[30] Foreign Application Priority Data

Nov. 27, 1987 [JP] Japan ................................ 62-297328
Nov. 27, 1987 [JP] Japan ................................ 62-297329
Dec. 25, 1987 [JP] Japan ................................ 62-326769
Dec. 25, 1987 [JP] Japan ................................ 62-326770

[51] Int. Cl.$^5$ .................. C07D 307/46; C07D 309/12
[52] U.S. Cl. .................................. 549/496; 549/214; 549/414; 549/472
[58] Field of Search ................. 549/496, 414, 214, 472

[56] References Cited

FOREIGN PATENT DOCUMENTS 2204584A 11/1988 United Kingdom .

OTHER PUBLICATIONS

Chemical Abstracts, vol. 106, No. 7, Feb. 16, 1987, p. 600, Abstract No. 49756x (Japanese Published Patent Appln. No. 61-140537).

Naruto et al., "Synthesis and Spasmolytic Activities of 2-(1,2-Benzisoxazol-3-((ω-(dialkylamino)alkoxy)-phenyl)acrylonitriles", Journal of Medicinal Chemistry, vol. 25, No. 10, Oct. 1982, pp. 1240–1245.

Primary Examiner—Nicky Chan
Attorney, Agent, or Firm—Sherman and Shalloway

[57] ABSTRACT

A phenoxypropyl derivative represented by the following formula

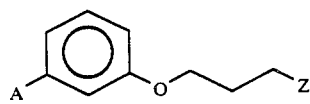
(I)

wherein A represents a formyl group, a protected formyl group, a hydroxymethyl group, a protected hydroxymethyl group, or a halomethyl group, and Z represents a halogen atom, an amino group, a phthalimide group or a group of the formula

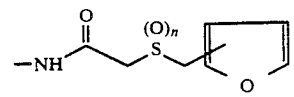

in which n is 0, 1 or 2.

6 Claims, No Drawings

PHENOXYPROPYL DERIVATIVES

This invention relates to novel phenoxypropyl derivatives. More specifically, it relates to phenoxypropyl derivatives represented by the following formula

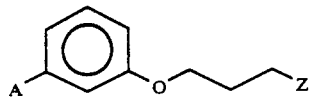
(I)

wherein A represents a formyl group, a protected formyl group, a hydroxymethyl group, a protected hydroxymethyl group, or a halomethyl group, and Z represents a halogen atom, an amino group, a phthalimide group or a group of the formula

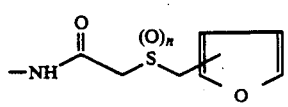

in which n is 0, 1 or 2.

The phenoxypropyl derivative of formula (I) is useful as an intermediate of a compound of the following formula

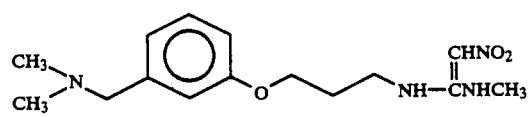
(A)

(see U. K. Patent Publications 1604674A and 1604675A) or a compound of the following formula

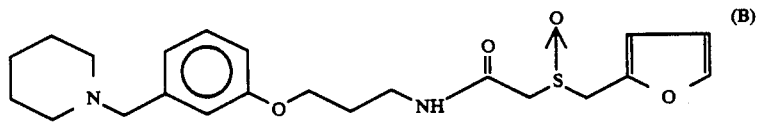
(B)

(see European Laid-Open Patent Publication No. 214823) which are useful as pharmaceuticals such as an antipeptic ulcer agent based on histamine $H_2$ receptor antagonizing activity.

The pharmaceutically effective compound of formula (A) or (B) has previously been produced by using an intermediate of the formula

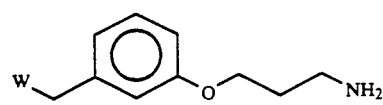
(E)

wherein W represents a disubstituted amino group, which is obtained by reacting a compound of the formula

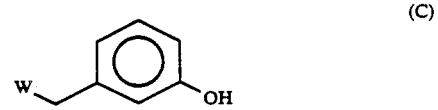
(C)

wherein W is as defined above, with a compound of the formula

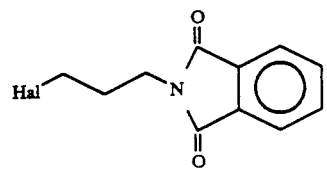
(D)

wherein Hal represents a halogen atom, and removing the phthalimide group from the product by hydrolysis.

The conventional method, however, does not give the intermediate in a sufficient yield, and is not industrially satisfactory.

In contrast, the compound of formula (I) provided by this invention can be produced easily in good yields from m-hydroxybenzaldehyde of formula (II) which is easily available commercially, as shown by the following Reaction Scheme. Moreover, the compound of formula (I) can be easily converted to a compound of formula (V) given below which has histamine $H_2$ receptor antagonizing activity and is useful as an antipeptic ulcer agent.

Reaction Scheme

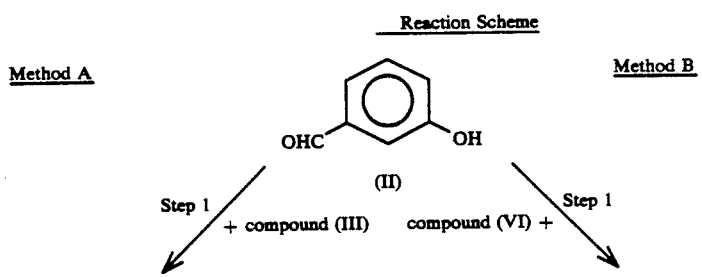

4,988,828
-continued
Reaction Scheme
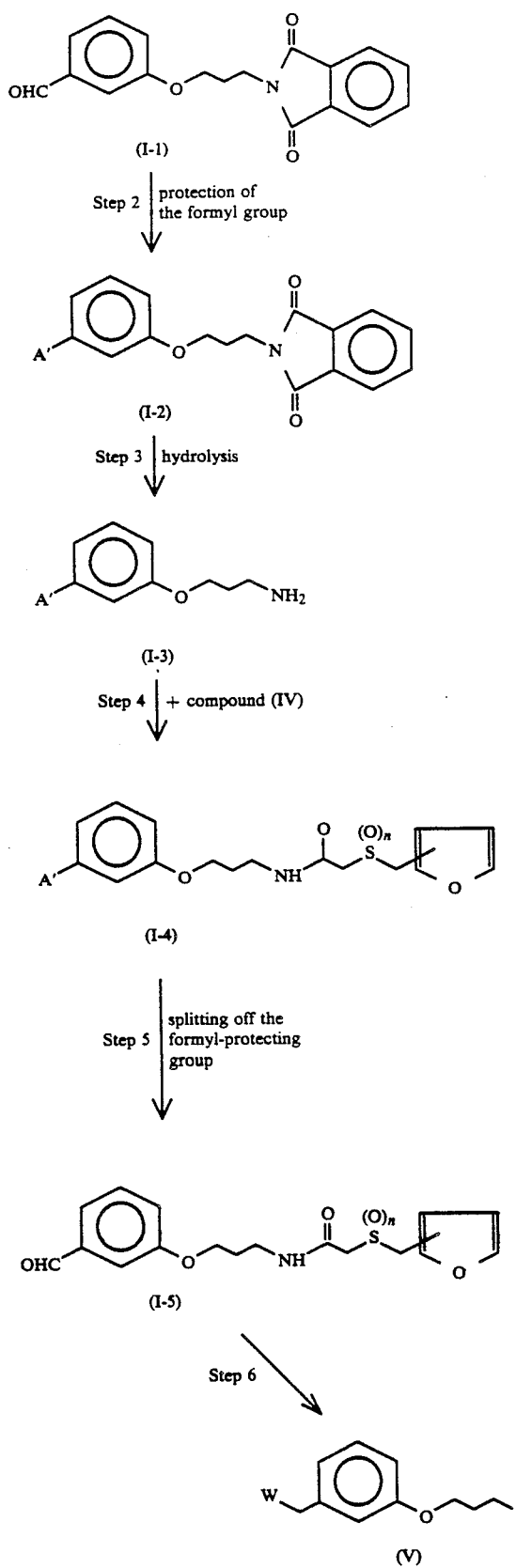
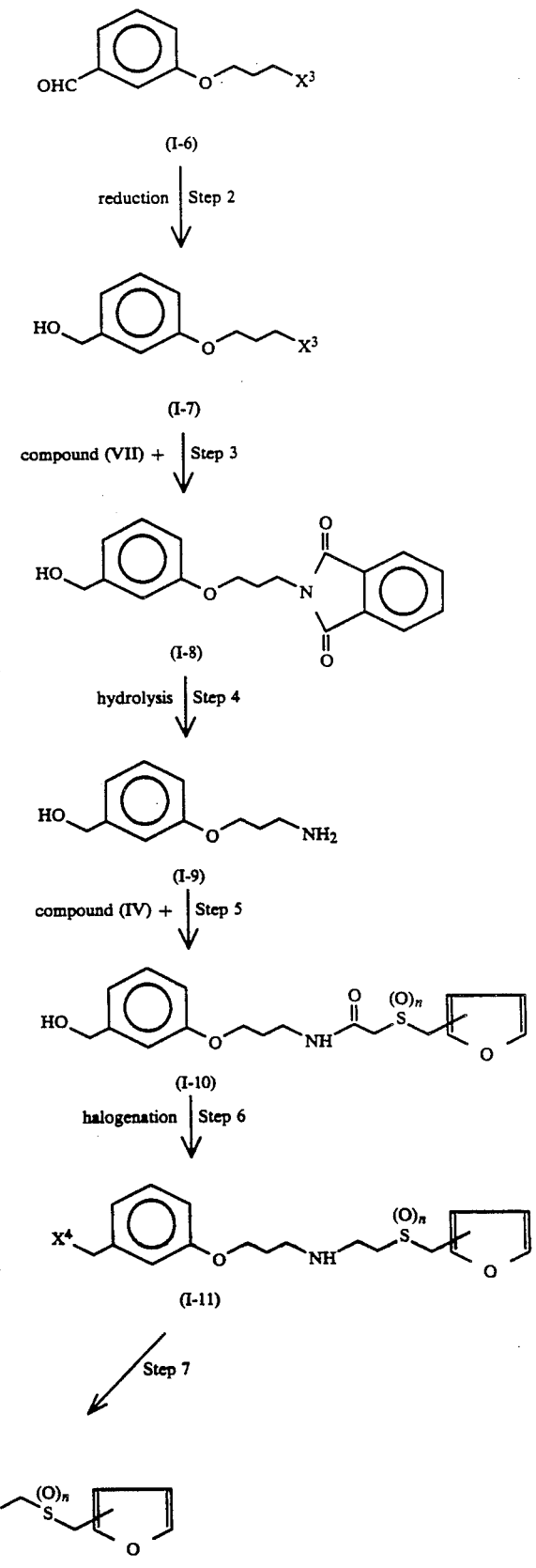

In the above Reaction Scheme, compounds (III), (IV), (VI) and (VII) have the following structural formulae.

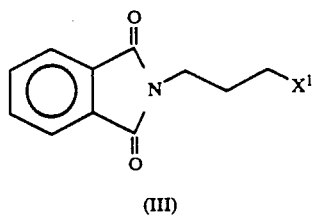

(III)

(IV)     (VI)

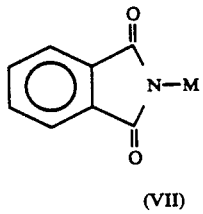

(VII)

In the Reaction Scheme and the above formulae, A' represents a protected formyl group; W represents a disubstituted amino group such as a dimethylamino, diethylamino, 1-pyrrolidinyl, piperidino, 1-perhydroazepinyl, 2-methylpiperidino, 3-methylpiperidino, 4-methyl-1-piperidino, 4-hydroxypiperidino, 1,2,5,6-tetrahydropyridin-1-yl, 4-methyl-1-piperazinyl, morpholino or thiomorpholino group; $X^1$ and $X^4$ each represent a halogen atom; $X^2$ and $X^3$ are identical or different and each represents a halogen atom; R represents an active ester residue such as a p-nitrophenyl, o-nitrophenyl, 2,4-dinitrophenyl or succinimide group; M represents a hydrogen atom or an alkali metal; and n is 0, 1 or 2.

In the present specification and the appended claims, the "protected formyl group" includes a formyl group protected by an ordinary known acetalization method by reaction with an alcohol. Specific examples include 1,3-dioxolan-2-yl, 1,4-dioxan-2-yl, dimethoxymethyl and diethoxymethyl groups. The 1,3-dioxolan-2-yl group which can be formed by reaction with ethylene glycol is preferred.

The "protected hydroxymethyl group" may be a hydroxymethyl group whose hydroxy moiety is protected by a known hydroxy-protective group. Specific examples of the protected hydroxymethyl group include tetrahydropyranyl, tetrahydrofuranyl, methoxymethyl, methoxyethyl, trimethylsilyl and triphenylmethyl groups. The methoxymethyl group is especially preferred.

The "halomethyl group" includes, for example, chloromethyl, bromomethyl and iodomethyl groups. The chloromethyl group is preferred.

A group represented by the following formula

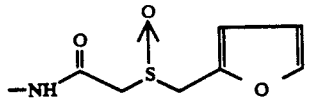

is a preferred example of the group of the following formula.

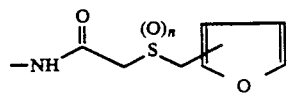

In the Reaction Scheme, the compounds of formulas (I-1) and (I-11) fall within the compound of formula (I) provided by this invention.

The methods of producing the compounds of this invention will be described below according to Methods A and B shown in the Reaction Scheme.

Method A

Step 1

In this step, m-hydroxybenzaldehyde of formula (II) is reacted with a propylphthalimide derivative of formula (III) to produce N-3-(3-formylphenoxy)-propyl]phthalimide of formula (I-1).

The compound of formula (II) as the starting material in this step is easily available commercially. The propylphthalimide derivative of formula (III) can be obtained by reacting phthalimide with a 1,3-dihalopropane. Examples of the compound of formula (III) are N-(3-bromopropyl)phthalimide and N-(3-chloropropyl)phthalimide.

The proportions of the starting compounds are not critical, and can be varied over a wide range depending upon the type of the compound (III), the reaction conditions, etc. Usually, it is convenient to use 1 to 1.5 moles, preferably 1.0 to 1.1 moles, of the compound of formula (III) per mole of the compound of formula (II).

This step is preferably carried out in the presence of a base such as an alkali metal compound. Examples of the alkali metal compound are alkali metal hydroxides such as sodium hydroxide and potassium hydroxide; alkali metal carbonates such as sodium carbonate and potassium carbonate; alkali metal hydrides such as sodium hydride and potassium hydride; alkali metal fluorides such as potassium fluoride, sodium fluoride and cesium fluoride; and sodium amide. The amount of the alkali metal compound used is not strictly limited. Generally, its suitable amount is 1 to 3 equivalents per mole of the propylphthalimide derivative of formula (III).

Desirably, the reaction in this step is carried out usually in a solvent. Suitable reaction solvents include, for example, aromatic hydrocarbons such as benzene, toluene and xylene; ethers such as ethyl ether, tetrahydrofuran (THF), dimethoxyethane (DME) and dioxane; amides such as dimethylformamide (DMF); sulfoxides such as dimethyl sulfoxide (DMSO); and nitriles such as acetonitrile and propionitrile.

The reaction temperature may generally be 0° to 200° C., preferably 70° to 100° C.

Step 2

In this step, N-[3-(3-formylphenoxy)propyl]phthalimide of formula (I-1) obtained in step 1 is reacted with an alcohol to give a phenoxypropylphthalimide derivative of formula (I-2) in which the formyl group is protected by acetalization.

The alcohol is used in this step as a protective group for the formyl group, and includes, for example, lower alcohols such as methanol (MeOH) and ethanol (EtOH), and glycols such as 1,2-ethylene glycol and 1,3-propylene glycol.

The alcohol may usually be used in an amount of 2 to 20 moles, preferably 2 to 10 moles, per mole of the compound of formula (I-1).

Preferably, this step is carried out in the presence of an acid. Examples of the acid are organic acids such as p-toluenesulfonic acid, malonic acid, oxalic acid and acetic acid; inorganic acids such as hydrochloric acid, phosphoric acid and sulfuric acid; and Lewis acids such as boron trifluoride/diethyl ether complex. The amount of the acid is not critical, but is desirably 1/10 to 3 equivalents per equivalent of the compound of formula (I-1).

Desirably, the reaction of this step is carried out in a solvent, for example aromatic hydrocarbons such as benzene and toluene, and halogenated hydrocarbons such as chloroform, carbon tetrachloride and methylene chloride.

The reaction can be carried out generally at a temperature of about 30° to 200° C., preferably 80° to 130° C. It is especially desirable to carry out the reaction under reflux using the solvent having a boiling point within this temperature range.

Step 3

In this step, the phthalimide group is split off from the phenoxypropylphthalimide derivative of formula (I-2) by hydrolysis to give a phenoxypropylamine derivative of formula (I-3).

Hydrolysis of the compound of formula (I-2) can be carried out by a known method, for example in the presence of a base. Examples of the base are inorganic bases such as hydrazine, sodium hydroxide, potassium hydroxide, sodium carbonate and potassium carbonate, and organic bases such as methylamine and ethylamine. The amount of the base used is not critical. Usually, it is used in an amount of 1 to 5 equivalents, preferably about 1 equivalent, per mole of the phenoxypropylphthalimide derivative of formula (I-2).

Usually, the hydrolysis can be carried out conveniently in water or a mixture of water and a water-miscible organic solvent at a temperature of about 30° to 100° C., preferably 30° to 80° C. Examples of the water-miscible organic solvent that can be used in this step are alcohols such as MeOH, EtOH and propanol (PrOH), and ethers such as ethyl ether, THF and DME.

Step 4

In this step, the phenoxypropylamine derivative of formula (I-3) obtained in step 3 is reacted with a furfurylthio ester derivative of formula (IV) to give a phenoxypropylamide derivative of formula (I-4).

This reaction can be generally carried out in a suitable solvent, for example aromatic hydrocarbons such as benzene, toluene and xylene, ethers such as ethyl ether, THF, DME and dioxane, amides such as DMF, and sulfoxides such as DMSO, at a temperature of about 0° to 50° C., particularly under mild temperature conditions around room temperature.

The proportion of the compound of formula (IV) with respect to the compound of formula (I-3) is not particularly limited. Usually, it is convenient to use the compound of formula (IV) in an amount of 1 to 3 moles, preferably 1.0 to 1.1 moles, per mole of the compound of formula (I-3).

The compound of formula (IV) to be reacted with the compound of formula (I-3) in the above reaction can be easily obtained, for example, by esterifying an acetic acid derivative of the following formula

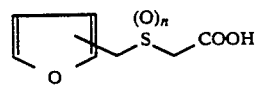

wherein n is as defined above. For example, when n is 1, the compound of formula (IV) can be obtained, for example, by reacting 2-(furfurylsulfinyl)acetic acid and nitrophenol in the presence of a dehydrocondensing agent such as dicyclohexylcarbodiimide.

Step 5

The phenoxypropylamide derivative of formula (I-4) obtained by step 4 is converted to a formylphenoxypropylacetamide derivative of formula (I-5) by subjecting it to a reaction of splitting off the formyl-protecting group.

The reaction of splitting off the formyl-protecting group may be carried out by any known method. For example, it can be carried out in the presence of an acid at a temperature of about 0° to 100° C., preferably 60° to 100° C., in a solvent, for example water, ketones such as acetone, alcohols such as MeOH, EtOH and PrOH, ethers such as THF, DME and dioxane, or nitriles such as acetonitrile.

Step 6

The formylphenoxypropylacetamide derivative of formula (I-5) produced as above can be converted to the compound of formula (V) having excellent histamine H2 receptor antagonizing activity by reacting it with a disubstituted amine of the formula $$WH \qquad (IX)$$

wherein W is as defined above.

This reaction is a so-called "reductive alkylation" whereby the compound of formula (I-5) is reacted with the compound of formula (IX) under reducing conditions to produce the compound of formula (V). It can be carried out in accordance with the ordinary reductive alkylation method. For example, the above reaction can be carried out by catalytic reduction under reducing conditions in the absence of a solvent, or in a solvent, for example an inert organic solvent such as an alcohol (e.g., MeOH, EtOH or PrOH), an ether (e.g., ethyl ether, THF and dioxane), or a halogenated hydrocarbon (e.g., chloroform and dichloromethane). The catalytic reduction is, for example, reduction with hydrogen in the presence of a hydrogenating catalyst such as platinum black, palladium-carbon or Raney nickel, hydrogenation with a complex metal hydride such as sodium borohydride, potassium cyanoborohydride and potassium borohydride, or reduction with nascent hydrogen, e.g. Zn/HCl. The reaction temperature is generally 0° C. to the refluxing temperature of the reaction mixture, preferably room temperature to 70° C. The amount of the compound of formula (IX) is 1 to 10 equivalents, preferably 1 to 2 equivalents, per mole of the compound of formula (I-5).

The compounds formed in the individual steps in the above method may be isolated and purified by known methods, such as acid base distribution, various types of chromatography, and recrystallization.

Method B

Step 1

In this step, m-hydroxybenzaldehyde of formula (II) which is commercially available is reacted with a 1,3-dihalopropane of formula (VI) which is also commercially available (such as 1-bromo-3-chloropropane or 1,3-dibromopropane) to give a formylphenoxypropane derivative of formula (I-6).

The above reaction can be advantageously carried out generally in the presence of a base in a solvent at a temperature of usually about 0° to 200° C., particularly 70° to 100° C. Examples of the solvent include aromatic hydrocarbons such as benzene, toluene and xylene, ethers such as ethyl ether, THF, DME and dioxane, amides such as DMF, sulfoxides such as DMSO, and nitriles such as acetonitrile and propionitrile. The base is preferably an alkali metal compound. Examples include alkali metal hydroxides such as sodium hydroxide and potassium hydroxide, alkali metal carbonates such as sodium carbonate and potassium carbonate, alkali metal hydrides such as sodium hydride and potassium hydride, sodium amide, potassium fluoride, sodium fluoride and cesium fluoride. The amount of the base is generally 1 to 3 equivalents per mole of the compound of formula (II).

The amount of the 1,3-dihalopropane of formula (VI) is not strictly limited, and can be varied depending upon its type or the reaction conditions used. Generally, it is desirable to use the 1,3-dihalopropane of formula (VI) in an amount of 1 to 10 moles, preferably 2 to 3 moles, per mole of the compound of formula (II).

Step 2

The formylphenoxypropane derivative of formula (I-6) obtained in step 1 is reduced to convert the formyl group into a hydroxymethyl group.

Reduction of the compound of formula (I-6) can be carried out by known reducing means. For example, it may be carried out using reducing reagents, for example metal hydride complex compounds such as sodium borohydride, lithium borohydride, zinc borohydride, lithium aluminum hydride, sodium aluminum hydride and sodium cyanoborohydride.

The reaction temperature is generally about −10° to 30° C., preferably 0° to 30° C.

Step 3

In this step, the hydroxyphenoxypropane derivative of formula (I-7) obtained in step 2 is reacted with phthalimide or its alkali metal salt of formula (VII) to give N-[3-(3-hydroxymethylphenoxy)propyl]phthalimide of formula (I-8). This step can be carried out by method (a) or (b) described below.

Method (a)

The compound of formula (I-7) is reacted with phthalimide in the presence of an organic ammonium salt, a crown ether and an inorganic base. Examples of the organic ammonium salt are tetra-n-butyl ammonium iodide, tetra-n-butyl ammonium bromide, tetra-n-butyl ammonium chloride and tetra-n-butyl ammonium hydrogen sulfate. Examples of the inorganic base are sodium hydroxide, potassium hydroxide, sodium carbonate and potassium carbonate. Examples of the crown ether are 12-crown-4 and 18-crown-6.

The suitable amounts of the organic ammonium salt and the inorganic base are 1/10 to 2 equivalents per mole of the compound of formula (I-7). The amount of the crown ether is 1/10 to 2 equivalents, per mole of the compound of formula (I-7).

Desirably, the reaction is carried out generally in a solvent. Examples of the solvent include aromatic hydrocarbons such as benzene, toluene and xylene, alcohols such as MeOH, EtOH and PrOH, ethers such as ethyl ether, THF, DME and dioxane, amides such as DMF, sulfoxides such as DMSO, and nitriles such as acetonitrile and propionitrile.

The suitable reaction temperature is generally about 60° to 120° C., preferably 80° to 100° C.

Conveniently, the phthalimide is used in an amount of generally 1 to 2 moles, preferably 1.0 to 1.1 moles, per mole of the compound of formula (I-7).

Method (b)

The compound of formula (I-7) is reacted with an alkali metal salt of phthalimide in the presence of an organic ammonium salt or a crown ether of the type and amount described above. A potassium or sodium salt may, for example, be used as the alkali metal salt of phthalimide.

The suitable reaction temperature is generally about 60° to 120° C., preferably 80° to 100° C. The alkali metal salt of phthalimide is conveniently used in an amount of generally 1 to 2 moles, preferably 1.0 to 1.1 moles, per mole of the compound of formula (I-7).

The hydroxymethyl group of the compound of formula (I-7) may be protected after step 3 so that subsequent steps may be carried out smoothly. By protecting the hydroxyl group in step 5 and allowing condensation reaction to proceed selectively with the amino group, the compound of formula (I-9) can be smoothly converted to the compound of formula (I-10).

Protective groups for the hydroxymethyl group may include, for example, tetrahydropyranyl, tetrahydrofuranyl, methoxymethyl, trimethylsilyl, dimethyl-t-butylsilyl and triphenylmethyl groups.

Introduction of tetrahydropyranyl and tetrahydrofuranyl groups as the protective groups can be carried out using 2,3-dihydro-4H-pyran and 2,3-dihydrofuran in the presence of an acid catalyst. These reagents are used suitably in an amount of generally 1 to 10 moles, preferably 1 to 1.5 moles, per mole of the compound of formula (I-7). The acid catalyst may be, for example, hydrochloric acid, sulfuric acid or p-toluenesulfonic acid. The suitable amount of the acid catalyst is 1/100 to 1/10 equivalent per mole of the compound of formula (I-7).

Desirably, the above reaction is carried out in a solvent. Examples of the solvent are aromatic hydrocarbons such as benzene, toluene and xylene, ethers such as ethyl ether, THF, DME and dioxane, amides such as DMF, and sulfoxides such as DMSO.

The reaction temperature is generally about −10° to 100° C., preferably 0° to 50° C.

Introduction of methoxymethyl, trimethylsilyl, dimethyl-t-butylsilyl and triphenylmethyl groups as the protective groups may be carried out using chloromethyl methyl ether, trimethylsilyl chloride, dimethyl-t-butylsilyl chloride and triphenylmethyl chloride in the presence of a base. The suitable amounts of these reagents are generally 1 to 10 moles, preferably 1 to 1.5 moles, per mole of the compound of formula (I-7).

Step 4

By hydrolyzing the compound of formula (I-8) obtained in step 3, the phthalimide group can be split off.

This hydrolysis can be carried out in the same way as the hydrolysis of the compound of formula (I-2) in step 3 of Method A.

Step 5

In this step, 3-(3-hydroxymethylphenoxy)propylamine of formula (I-9) produced in step 4 is reacted with a furfurylthio ester derivative of formula (IV) to convert it into a hydroxyemthylphenoxypropylacetamide derivative of formula (I-10).

The reaction of the compound of formula (I-9) with the compound of formula (IV) can be carried out in the same way as in the reaction of the compound of formula (I-3) with the compound of formula (IV) in step 4 of Method A.

Step 6

By halogenating the compound of formula (I-10) obtained in step 5, it can be converted to a halogenomethylphenoxypropylamide derivative of formula (I-11).

This halogenation can be carried out, for example, by treating the compound of formula (I-10) with a halogenating agent. Examples of the halogenating agent are phosphorus pentabromide, phosphorus oxybromide, methanesulfonyl bromide, thionyl chloride, p-toluenesulfonyl chloride, methanesulfonyl chloride, phosphorus oxychloride, phosphorus pentachloride and phosphorus trichloride.

The amount of the halogenating agent used may be varied depending upon its type. Generally, it is proper to use it in a proportion of 1 to 2 equivalents, preferably 1.0 to 1.2 equivalents, per mole of the compound of formula (I-10).

The halogenating reaction is desirably carried out in the presence of a base. Examples of the base include organic bases such as triethylamine and pyridine; and inorganic bases such as anhydrous potassium carbonate and anhydrous sodium hydrogen carbonate. The amount of the base used is preferably 1.0 to 1.2 equivalents per mole of the halogenating agent.

The above reaction may be carried out in the absence of solvent. Usually, it is desirably carried out in a solvent. Examples of the solvent are aromatic hydrocarbons such as benzene, toluene and xylene, ethers such as ethyl ether, THF, DME and dioxane, amides such as DMF, and sulfoxides such as DMSO.

The reaction temperature may be generally about −10° to 50° C., preferably −10° to 20° C.

Step 7

The compound of formula (I-11) obtained by step 6 can be converted to the compound of formula (V) useful as a drug having excellent histamine $H_2$ receptor antagonizing activity by reacting it with a disubstituted amine of formula (IX).

The reaction of the compound of formula (I-11) with the compound of formula (IX) can be easily carried out by using the compound of formula (IX) in an amount of 2 to 10 equivalents, preferably 2 to 5 equivalents, per mole of the compound of formula (I-11) and an organic or inorganic base in an amount of 1 to 10 equivalents, preferably 1 to 5 equivalents, per mole of the compound of formula (I-11). Generally, the reaction can be carried out in the absence of solvent or in a suitable solvent.

The solvent, the inorganic base and the reaction temperature employed in this reaction may be the same as those described in step 1. Examples of the organic base are triethylamine and pyridine.

The products obtained in the individual steps of Method B may be isolated and purified by known means such as acid base distribution, various types of chromatography and recrystallization.

EXAMPLE 1

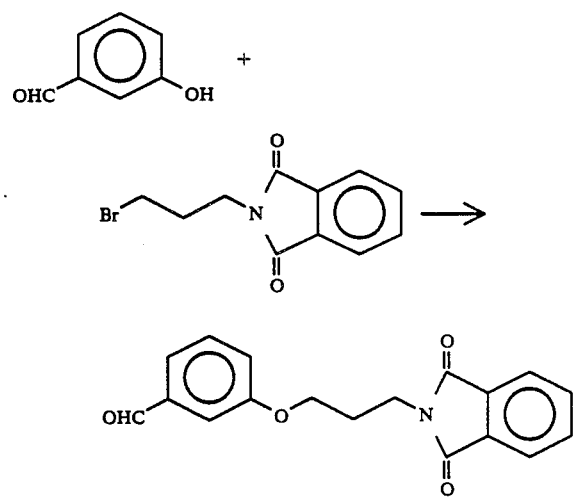

N-3-(3-formylphenoxy)propylphthalimide m-Hydroxybenzaldehyde (12.2 g), N-(3-bromopropyl)phthalimide (26.8 g), anhydrous potassium carbonate (13.8 g) and potassium iodide (1.7 g) were suspended in acetonitrile (600 ml), and the suspension was heated under reflux for 18 hours. After cooling, the precipitate was removed, and the solvent was evaporated under reduced pressure. The residue was distributed between benzene and water. The organic layer was washed successively with a 1N aqueous NaOH solution, water and a saturated aqueous solution of sodium chloride, and dried over anhydrous magnesium sulfate. The solvent was evaporated under reduced pressure to give 29.16 g (yield 94%) of N-[3-(3-formylphenoxy)-propyl]phthalimide as crystals.

Melting point: 103.3°–104.0° C.

$^1$H-NMR (δ, CDCl$_3$): 99.3(1H, s), 7.80–7.90(2H, m), 7.66–7.76(2H, m), 7.41–7.46 (1H, m), 7.39(1H, t, J=7.3 Hz), 7.28(1H, s), 7.06(1H, dd, J=7.3, 2.0 Hz), 4.10(2H, t, J=5.8 Hz), 3.93(2H, t, J=6.8 Hz), 2.22(2H, tt, J=6.8, 5.8 Hz).

IR (cm$^{-1}$, KBr): 2728, 1764, 1690, 1602, 1590, 1260.

Mass: for C$_{18}$H$_{15}$NO$_4$. Calculated 309.1002. Found: 309.1011.

EXAMPLE 2

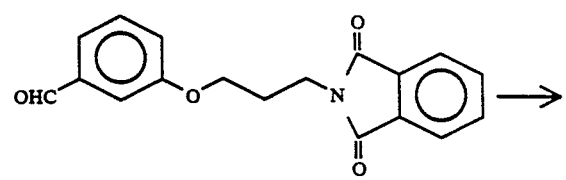

-continued

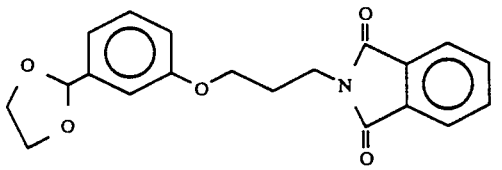

N-{3-[3-(1,3-dioxolan-2-yl)phenoxy)propyl}-phthalimide

N-[3-(3-formylphenoxy)propyl]phthalimide (29 g) was dissolved in 400 ml of benzene, and 11.67 g of ethylene glycol and 1.8 g of p-toluenesulfonic acid were added, and the mixture was heated under reflux for 7 hours while water was removed by using a Dean-Stark trap. After the reaction, the reaction mixture was cooled and the benzene layer was washed successively with a 1N aqueous NaOH solution, water, and a saturated aqueous solution of sodium chloride and dried over anhydrous magnesium sulfate. The solvent was removed under reduced pressure to give 30.63 g (yield 92%) of N-{3-[3-(1,3-dioxolan-2-yl)phenoxy]-propyl}phthalimide.

$^1$H-NMR (δ, CDCl$_3$): 7.80–7.90(2H, m), 7.65–7.75 (2H, m), 7.25(1H, d, J=7.5 Hz), 7.30 (1H, d, J=7.5 Hz), 6.39(1H, s), 6.81 (1H, d, J=7.5 Hz), 5.76(1H, s), 3.98–4.16(4H, m), 4.05(2H, t, J=5.8 Hz), 3.91(2H, t, J=7.6 Hz), 2.18 (2H, tt, J=7.6, 5.8 Hz).

IR (cm$^{-1}$, KBr): 2956, 1774, 1712, 1608, 1590, 1406.

Mass for C$_{20}$H$_{19}$NO$_5$: Calculated: 353.1262. Found: 353.1257.

EXAMPLE 3

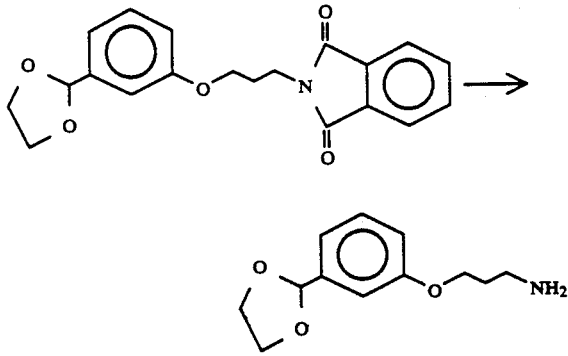

3-[3-(1,3-dioxolan-2-yl)phenoxy]propylamine

N-{3-3-(1,3-dioxolan-2-yl)phenoxy)propyl}phthalimide (30.27 g) and hydrazine hydrate (6.48 g) were dissolved in 400 ml of methanol, and the solution was heated under reflux for 2 hours. The solvent was then removed under reduced pressure, and the precipitated solid was separated by filtration. The solid was washed with methylene chloride. The filtrate and the washing were combined, and the solvent was evaporated. Methylene chloride was added to the residue, and the operation was repeated until there was no turbidity. Thus, 16.78 g (yield 88%) of 3-[3-(1,3-dioxolan-2-yl)phenoxy]-propylamine was obtained.

$^1$H-NMR (δ, CDCl$_3$): 7.28(1H, t, J=7.8 Hz), 7.05 (1H, d, J=7.8 Hz), 7.04(1H, s), 6.89 (1H, d, J=7.8 Hz), 5.78(1H, s), 3.98–4.15(4H, m), 4.06(2H, t, J=5.0 Hz), 2.95(2H, t, J=6.8 Hz), 2.64 (2H, br-s), 1.97(2H, tt, J=6.8, 5.0 Hz).

IR (cm$^{-1}$, film): 3384, 2925, 1590, 1274.

Mass: for C$_{12}$H$_{17}$NO$_5$: Calculated: 223.1208. Found: 223.1216.

EXAMPLE 4

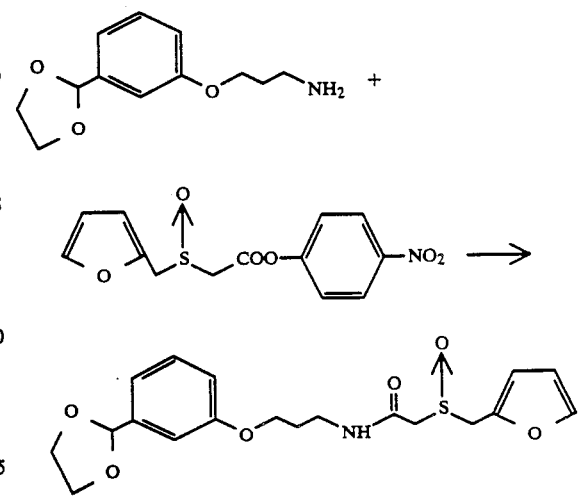

N-{3-[3-(1,3-dioxolan-2-yl)phenoxy]propyl}-2-(furfurylsulfinyl)acetamide

3-[3-(1,3-dioxolan-2-yl)phenoxy]propylamine (16.3 g) was dissolved in 400 ml of methylene chloride, and p-nitrophenyl 2-(furfurylsulfinyl)acetate (22.58 g) was added little by little. The mixture was stirred at room temperature for 18 hours. The organic layer was washed successively with a 1N aqueous NaOH solution and water and dried over anhydrous magnesium sulfate. The solvent was evaporated to give 21.29 g (yield 74%) of N-{3-[3-(1,3-dioxolan-2-yl)phenoxy]propyl}-2-(furfurylsulfinyl)acetamide.

Melting point: 95.3°–96.1° C.

$^1$H-NMR (δ, CDCl$_3$): 7.43(1H, d, J=2.5 Hz), 7.28(1H, t, J=7.7 Hz), 7.06(1H, d, J=7.7 Hz), 7.04(1H, d, J=2.4 Hz), 6.92(1H, dd, J=7.7, 2.4 Hz), 6.45 (1H, d, J=3.4 Hz), 6.39(1H, dd, J=3.4, 2.5 Hz), 5.78(1H, s), 4.25(1H, d, J=14.2 Hz), 4.15(1H, d, J=14.2 Hz), 3.98–4.25(4H, m), 4.06(2H, t, J=5.8 Hz), 3.56(1H, d, J=14.2 Hz), 3.52(2H, dt, J=6.1, 6.5 Hz), 3.31(1H, d, J=14.2 Hz), 2.03(2H, tt, J=6.5, 5.8 Hz).

IR (cm$^{-1}$, KBr) 1658, 1610, 1568, 1270, 1016.

Mass: C$_{19}$H$_{23}$NO$_6$S: Calculated: 393.1245. Found 393.1237.

EXAMPLE 5

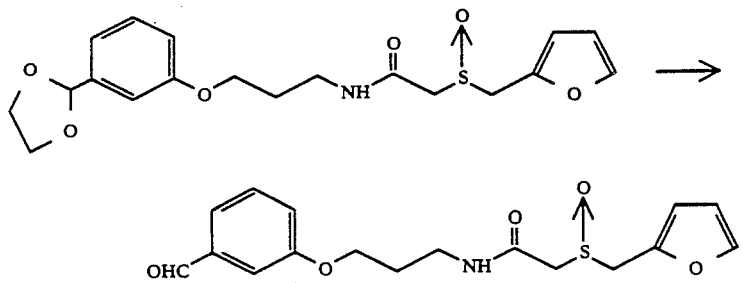

N-[3-(3-formylphenoxy)propyl]-2-(furfurylsulfinyl)acetamide

N-{3-[3-(1,3-dioxolan-2-yl)phenoxy]propyl}-2-(furfurylsulfinyl)acetamide (20 g) was dissolved in 300 ml of acetone, and 60 ml of a 1N aqueous solution of HCl was added. The mixture was heated under reflux for 8 hours. After cooling, the solution was neutralized with a saturated aqueous solution of sodium hydrogen carbonate, concentrated and extracted with ethyl acetate. The organic layer was washed with water, and dried over anhydrous magnesium sulfate. The solvent was evaporated to give 17 g (yield 81%) of N-[3-(3-formylphenoxy)propyl]-2-(furfurylsulfinyl)acetamide.

$^1$H-NMR (δ, CDCl$_3$): 9.96(1H, s), 7.09–7.65 (6H, m), 6.46(1H, d, J=2.6 Hz), 6.40(1H, dd, J=2.6, 2.0 Hz), 4.25 (1H, d, J=14.4 Hz), 4.16(1H, d, J=14.4 Hz), 4.10(2H, t, J=5.8 Hz), 3.58(4H, d, J=14.3 Hz), 3.54(2H, dt, J=5.7, 6.5 Hz), 2.07(2H, tt, J=5.8, 6.5 Hz).

IR (cm$^{-1}$, film): 1696, 1664, 1266, 1072.

Mass: for C$_{17}$H$_{12}$NO$_5$S: Calculated: 349.0984. Found: 349.0988.

EXAMPLE 6

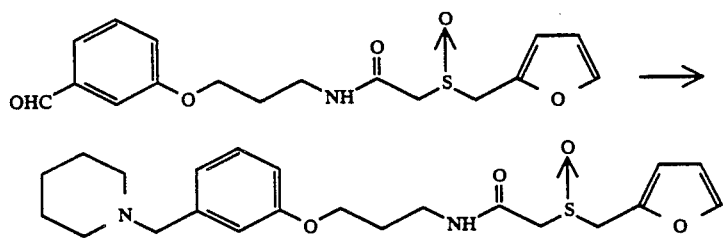

N-{3-[-3-(piperidinomethyl)phenoxy]propyl}-2-(furfurylsulfinyl)acetamide

N-[3-(3-formylphenoxy)propyl]-2-(furfurylsulfinyl)acetamide (13.85 g) was dissolved in 150 ml of ethanol, and while 5.06 g of piperidine was added dropwise, the mixture was stirred at room temperature for 15 hours. The reaction solution was cooled with ice, and 1.5 g of sodium borohydride was added. The mixture was stirred for 5 hours. 1N-HCl was added to the reaction solution to make it acidic, and the solvent was evaporated. The residue was poured into water and extracted with ethyl acetate. The aqueous layer was made basic by adding anhydrous sodium carbonate, and extracted with ethyl acetate. The organic layer was washed successively with water and a saturated aqueous solution of sodium chloride, and dried over anhydrous magnesium sulfate. The solvent was evaporated, and the residue was purified by silica gel column chromatography (eluent: chloroform/methanol=95/5) to give 8.80 g (yield 53%) of N-{3-[3-(piperidinomethyl)phenoxy] propyl}-2-(furfurylsulfinyl) acetamide.

$^1$H-NMR (δ, CDCl$_3$): 7.43(1H, d, J=1.5 Hz), 6.75–7.30(5H, m), 6.46(1H, d, J=1.5 Hz), 6.39(1H, d, J=1.5 Hz), 4.26(1H, d, J=14.2 Hz), 4.16(1H, d, J=14.2 Hz), 4.05(2H, t, J=6.3 Hz), 3.58(1H, d, J=14.2 Hz), 3.55(2H, dt, J=6.3, 6.3 Hz), 3.44(2H, s), 3.31(1H, d, J=14.2 Hz), 2.30-2.50(4H, m), 2.04 (2H, tt, J=6.3, 6.3 Hz), 1.40-1.70 (6H, m).

IR (cm$^{-1}$, KBr) 1660, 1020.

Mass: for C$_{22}$H$_{30}$N$_2$O$_4$S: Calculated: 418.1926. Found: 418.1922.

EXAMPLE 7

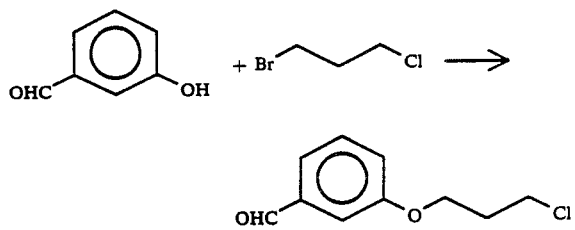

m-(3-Chloropropyloxy)benzaldehyde m-Hydroxybenzaldehyde (10 g), 1-bromo-3-chloropropane (13 g) and potassium carbonate (14 g) were suspended in 300 ml of acetonitrile, and the suspension was refluxed for 18 hours. After cooling, the insoluble matter was removed by filtration. The filtrate was concentrated, and the residue was taken into ethyl acetate, washed with water and dried. The solvent was evaporated to give 15.8 g (yield 97.1%) of m-(3-chloropropyloxy)benzaldehde $^1$H-NMR (δ, CDCl$_3$): 9.98(1H, s), 7.15–7.51 (4H, m), 4.19(2H, t, J=5.9 Hz), 3.76 (2H, t, J=6.4 Hz), 2.27 (2H, tt, J=6.4, 5.9 Hz).

IR (cm$^{-1}$, film) 1698, 1602, 1264.

Mass: for C$_{10}$H$_{11}$ClO$_2$: Calculated: 198.0447. Found: 199.0442.

EXAMPLE 8

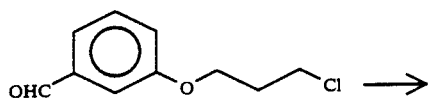

m-(3-Chloropropyloxy)benzyl alcohol m-(3-Chloropropyloxy)benzaldehyde (15 g) was dissolved in 200 ml of ethanol. With ice cooling, 1.5 g of sodium borohydride was added little by little. Two hours later, the excess of the hydride was decomposed with 5% hydrochloric acid, followed by concentration. The residue was extracted with ethyl acetate, and dried. The solvent was evaporated to give 15 g of m-(3-chloropropyloxy)benzyl alcohol quantitatively.

$^1$H-NMR ($\delta$, CDCl$_3$): 7.28(1H, t, J=7.6 Hz), 6.94(1H, d, J=7.6 Hz), 6.93(1H, s), 6.84(1H, d, J=7.6 Hz), 4.67(2H, s), 4.13(2H, t, J=5.8 Hz), 3.75(2H, t, J=6.4 Hz), 2.24(2H, tt, J=6.4, 5.8 Hz), 1.67(1H, br-s).

IR (cm$^{-1}$, film) 3356, 1604, 1266.

Mass: for C$_{10}$H$_{13}$ClO$_2$. Calculated: 200.0604. Found: 200.0600.

EXAMPLE 9

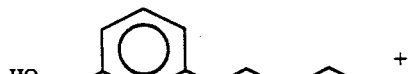
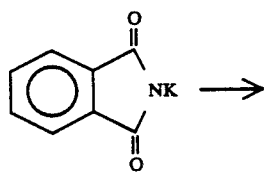
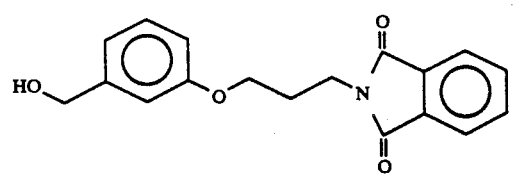

N-[3-(3-hydroxymethylphenoxy)propyl]phthalimide m-(3-Chloropropyloxy)benzyl alcohol (14 g), phthalimide potassium salt (13 g) and tetra-n-butyl ammonium hydrogen sulfate (2 g) were suspended in 200 g of acetonitrile. The suspension was refluxed for 18 hours. After cooling, the insoluble matter was removed by filtration, and the filtrate was concentrated. The concentrate was taken into ethyl acetate, washed with a 1N aqueous solution of sodium hydroxide and water, and then dried. The solvent was evaporated, and the residue was recrystallized from ethanol to give 16.7 g (yield 76.9%) of N-[3-(3-hydroxymethylphenoxy)propyl]phthalimide.

$^1$H-NMR ($\delta$, CDCl$_3$): 7.80–7.85(2H, m), 7.45–7.69(2H, m), 7.21(1H, t, J=7.8 Hz), 6.91(1H, d, J=7.8 Hz), 6.82(1H, d, J=2.5 Hz), 6.72(1H, dd, J=7.8, 2.5 Hz), 4.62(2H, s), 4.04 J=6.8 Hz), 2.18(2H, tt, J=6.8, 5.7 Hz), 1.74 (1H, br-s).

IR (cm$^{-1}$, KBr) 3528, 1772, 1712, 1612, 1254.

Mass: for C$_{18}$H$_{17}$NO$_4$: Calculated: 311.1157. Found: 311.1156.

EXAMPLE 10

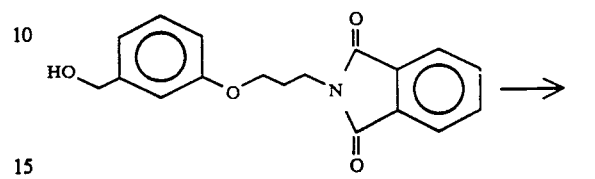
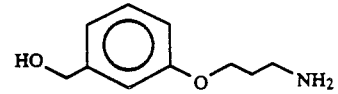

3-(3-Hydroxymethylphenoxy)propylamine

N-[3-(3-hydroxymethylphenoxy)propyl]phthalimide (16 g) was dissolved in 300 ml of methanol, and 5 g of hydrazine hydrate was added. The mixture was refluxed for 5 hours, and after cooling, the insoluble matter was removed by filtration. The filtrate was concentrated to give 4.85 g (yield 52.1%) of 3-(3-hydroxymethylphenoxy)propylamine.

$^1$H-NMR ($\delta$, CDCl$_3$): 7.24(1H, d, J=7.6 Hz), 6.92(1H, s), 6.91(1H, d, J=7.6 Hz), 6.79(1H, d, J=7.6 Hz), 4.63(2H, s), 4.01(2H, t, J=5.8 Hz), 2.85(2H, t, J=6.8 Hz), 2.05-2.30(3H, br-s), 1.89 (2H, tt, J=5.8, 6.8 Hz).

IR (cm$^{-1}$, KBr): 3352, 1604, 1266.

Mass for C$_{10}$H$_{15}$NO$_2$. Calculated 181.1103. Found: 181.1111.

EXAMPLE 11

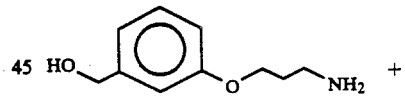
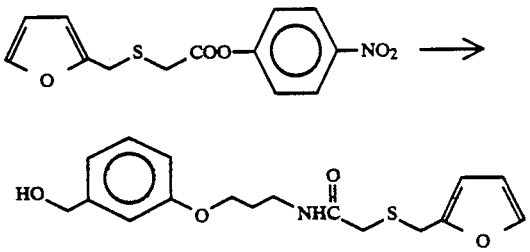

N-[3-(3-hydroxymethylphenoxy)propyl-]2-(furfurylthio)acetamide p-Nitrophenyl 2-(furfurylthio)acetate (6.5 g) was dissolved in 200 ml of tetrahydrofuran, and under ice cooling, 75 ml of a tetrahydrofuran solution of 4 g of 3-(3-hydroxymethylphenoxy)propylamine was added dropwise to the solution. One hour later, the temperature was returned to room temperature, and the mixture was stirred for 18 hours. The solvent was concentrated, and the concentrate was taken into ethyl acetate, washed with a 1N aqueous solution of sodium hydroxide and water, and dried. The solvent was evaporated to give 7.02 g (94.9%) of N-3-(3-hydroxymethylphenoxy)-propyl]-2-(furfurylthio)acetamide.

$^1$H-NMR (δ, CDCl$_3$): 7.33(1H, d, J=2.0 Hz), 7.27(1H, d, J=7.8 Hz), 6.97(1H, s), 6.95(1H, d, J=7.8 Hz), 6.86(1H, d, J=7.8 Hz), 6.28(2H, dd, J=3.7, 2.0 Hz), 6.18(1H, d, J=3.7 Hz), 4.68(2H, s), 4.05(2H, t, J=6.0 Hz), 3.73(2H, s), 3.43(2H, dt, J=6.5, 6.5 Hz), 3.22 (2H, s), 1.99(2H, tt, J=6.5, 6.0 Hz), 1.75–1.85(1H, br-s).

IR (cm$^{-1}$, ): 3292, 1636, 1610, 1258, 1154, 1050.

Mass: for C$_{17}$H$_{21}$NO$_4$S. Calculated: 338.1191. Found: 335.1183.

EXAMPLE 12

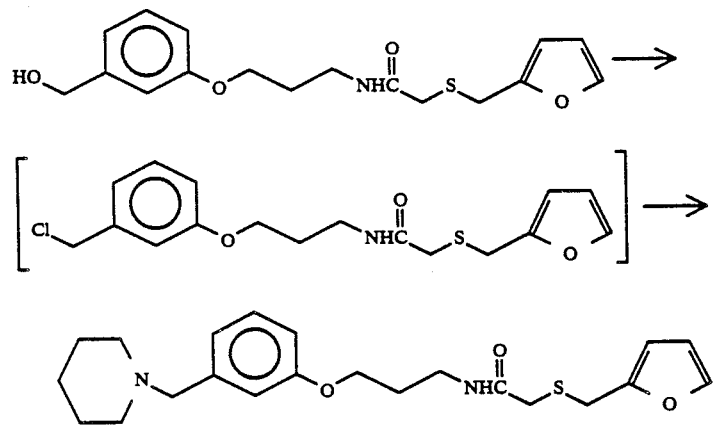

N-{3-[3-(piperidinomethyl)phenoxy]propyl}-2-(furfurylthio)acetamide

N-[3-(3-hydroxymethylphenoxy)propyl]-2-(furfurylthio)acetamide (6.5 g) and triethylamine (4 g) were dissolved in 200 ml of chloroform. Under ice cooling, 2.8 g of thionyl chloride was added dropwise to the solution. The mixture was stirred for 3 hours, and then the solution was washed with a saturated aqueous solution of sodium hydrogen carbonate and water, and dried. The solvent was evaporated, and the residue was dissolved in 250 ml of ethanol and refluxed with 5 g of piperidine. Five hours later, the reaction solution was concentrated. The residue was taken into ethyl acetate and washed with 5% HCl. The washing (aqueous layer) was made alkaline with potassium carbonate (solid), and again extracted with ethyl acetate. The extract was washed with water and dried. The solvent was evaporated to give 5.09 g (yield 65.3%) of N-(3-[3-(piperidinomethyl)phenoxy]propyl)-2-(furfurylthio)acetamide.

$^1$H-NMR (δ, CDCl$_3$): 7.15–7.40(3H, m), 6.75–7.00(3H, m), 6.18–6.28(2H, m), 4.05(2H, t, J=6.0 Hz), 3.73(2H, s), 3.44(2H, s), 3.43(2H, t, J=6.0 Hz), 3.23(2H, s), 2.30–2.45(4H, m), 1.99 (2H, tt, J=6.0, 6.0 Hz), 1.40–1.70 (6H, m).

IR (cm$^{-1}$, film): 1655.

Mass: for C$_{22}$H$_{30}$N$_2$O$_3$S. Calculated: 402.1977. Found: 402.1972.

EXAMPLE 13

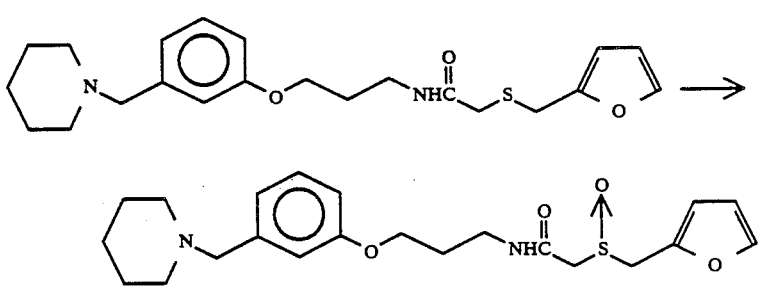

N-{3-[3-(piperidinomethyl)phenoxy]propyl}-2-(furfurylsulfinyl)acetamide

Five grams of N-(3-3-(piperidinomethyl)-phenoxy)-propyl}-2-(furfurylthio)acetamide was dissolved in 150 ml of dichloromethane, and under ice cooling, 50 ml of a dichloromethane solution of 3 g of m-chloroperbenzoic acid was added dropwise to the solution. The mixture was stirred for 3 hours, and the reaction solution was washed with 5% HCl. The washing (aqueous layer) was made alkaline with potassium carbonate (solid). The alkaline solution was extracted with ethyl acetate. The extract was washed with water, and dried. The solvent was evaporated to give 2.35 g (yield 45.2%) of N-{3-[3-(piperidinomethyl)phenoxy]propyl}-2-(furfurylsulfinyl)acetamide.

$^1$H-NMR (δ, CDCl$_3$): 7.43(1H, d, J=1.5 Hz), 6.75–7.30(5H, m), 6.46(1H, d, J=1.5 Hz), 6.39(1H, d, J=1.5 Hz), 4.26(1H, d, J=14.2 Hz), 4.16(1H, d, J=14.2 Hz), 4.05(2H, t, J=6.3 Hz), 3.58(1H, d, J=14.2 Hz), 3.55(2H, dt, J=6.3, 6.3 Hz), 3.44(2H, s), 3.31(1H, d, J=14.2 Hz), 2.30–2.50 (4H, m), 2.04(2H, tt, J=6.3, 6.3 Hz), 1.40–1.70(6H, m).

IR (cm$^{-1}$, KBr): 1660, 1020.

Mass: for $C_{22}H_{30}N_2O_4S$. Calculated: 418.1926. Found: 418.1922.

TEST EXAMPLE 1

Histamine $H_2$ antagonizing activity

Hartley-strain guinea pigs (male, weight 300 to 350 g) were killed by a blow on the head, and the heart was extracted. The right atrium was isolated in the Krebs-Henselite solution through which a mixed gas ($O_2$ 95%, $CO_2$ 5%) was circulated. The right atrium was suspended in an organ bath (30 ml) filled with the Krebs-Henselite solution kept at 32° C. The mixed gas was circulated through the organ bath, and a diastolic tension of 1 g was maintained. Contraction of the right atrium was recorded by a force-displacement transducer, and the heart rate was counted by a heart rate meter interlocked with the transducer.

Histamine (used in the form of dihydrochloride) was added cumulatively to the organ bath in a concentration of $1\times 10^{-8}M$ to $3\times 10^{-5}M$. Thus, the dose-response curve of histamine was obtained. The inside of the organ bath was washed several times, and the test compound ($1\times 10^{-6}$, $1\times 10^{-7}M$) was added to the organ bath. Ten minutes later, the dose-response curve of histamine in the presence of the test compound was obtained.

The $pA_2$ value of the test compound was determined from the first histamine dose-response curve and the histamine dose-response curve in the presence of the test compound by the method of J. M. Van Rossum (Arch. Int. Pharmacodyn. Ther., 143-299, 1963).

The results are shown below.

| Test compound | $pA_2$ |
| --- | --- |
| Example 12 | 7.3 |
| Example 13 | 7.1 |

For comparison, cimetidine was used, and its $pA_2$ was measured by the same procedure as above and found to be 6.5.

TEST EXAMPLE 2

Gastric mucosal protecting activity

Male Donryu rats (150 to 250 g) which had been caused to fast for 24 hours were used. The test compound was administered in a dose of 10 mg/kg. p.o., and 30 minutes later, a necrotizing substance (0.4N-HCl+50% ethanol) was administered orally in a dose of 5 ml/kg. One hour after the administration of the necrotizing substance, the stomach was dissected out and fixed with formalin. The area of ulcer which occurred was measured, and by comparison with a control group, the percent inhibition of the test compound was determined. The results are shown below.

| Test compound | Percent inhibition |
| --- | --- |
| Example 12 | 63 |
| Example 13 | 72 |

For comparison, cimetidine was used, and its percent inhibition was determined by the same procedure as above. No inhibition was observed in a dose of 10 mg/kg p.o., and at a dose of 30 mg/kg p.o., its percent inhibition was 11%.

We claim:

1. A phenoxypropyl derivative represented by the following formula

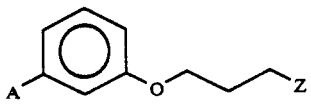

(I)

wherein A represents a hydroxymethyl group, a protected hydroxymethyl group, or a halomethyl group, and Z represents a group of the formula

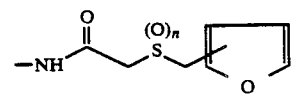

in which n is 0, 1 or 2.

2. The compound of claim 1 in which the protected hydroxymethyl group is a methoxymethyl group.

3. The compound of claim 1 in which the halomethyl group is a chloromethyl group.

4. The compound of claim 1 in which Z is

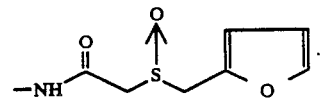

5. The compound of claim 1 in which A is a hydroxymethyl group and Z is a group of the formula

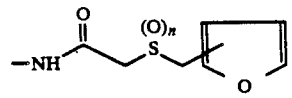

in which n is 0, 1 or 2.

6. The compound of claim 5 in which n is 0.

* * * * *